US006063784A

United States Patent [19]

Bigg et al.

[11] Patent Number: 6,063,784

[45] Date of Patent: May 16, 2000

[54] HETEROARYLOXYETHYLAMINES, METHOD OF PREPARATION, APPLICATION AS MEDICINE AND PHARMACEUTICAL COMPOSITIONS CONTAINING THEM

[75] Inventors: Dennis Bigg, Gif-sur-Yvette; Marie-Odile Galcera, Bondoufle, both of France

[73] Assignee: Societe de Conseils de Recherches et D'Applications Scientifiques (S.C.R.A.S.), France

[21] Appl. No.: 09/254,787

[22] PCT Filed: Sep. 26, 1997

[86] PCT No.: PCT/FR97/01691

§ 371 Date: Mar. 10, 1999

§ 102(e) Date: Mar. 10, 1999

[87] PCT Pub. No.: WO98/13349

PCT Pub. Date: Apr. 2, 1998

[30] Foreign Application Priority Data

Sep. 27, 1996 [FR] France .................................. 96 11798

[51] Int. Cl.[7] ...................... C07D 215/00; C07D 215/28; C07D 215/20; A61K 31/47; A61K 31/495

[52] U.S. Cl. .......................... 514/249; 546/166; 546/178; 546/181; 546/157; 544/353; 514/311; 514/312

[58] Field of Search .................................... 546/166, 178, 546/181, 157; 544/353; 514/249, 311, 312

[56] References Cited

FOREIGN PATENT DOCUMENTS 0512755 11/1992 European Pat. Off. .

9203426 3/1992 WIPO .

9631461 10/1996 WIPO .

OTHER PUBLICATIONS

Ross, Chapter 2 in Goodman and Gilman's The Pharmacological Basis of Therapeutics, 8th Ed., Pergamon Press, P.33–35, 1991.

Brayer et al. Chem. abstract 114:121758, Nov. 1991.

Chilmonczyk et al Buspirone . . . Analogues, Journal of Medicinal Chemistry, vol. 38, No. 10, May 12, 1995, pp. 1701–1710.

Hibert et al, Graphics . . . Receptor, Journal of Medicinal Chemistry, vol. 31, No. 6, 1988, pp. 1087–1093.

*Primary Examiner*—Richard L. Raymond
*Assistant Examiner*—Hong Liu
*Attorney, Agent, or Firm*—Bierman, Muserlian and Lucas

[57] ABSTRACT

A compound selected from the group consisting of a compound of the formula

I

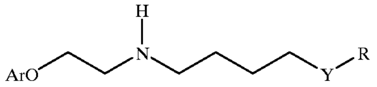

wherein the substituents are defined as in the application and its non-toxic, pharmaceutically acceptable acid addition salts which are useful for treating hypertension.

10 Claims, No Drawings

HETEROARYLOXYETHYLAMINES, METHOD OF PREPARATION, APPLICATION AS MEDICINE AND PHARMACEUTICAL COMPOSITIONS CONTAINING THEM

This application is a 371 of PCT FR97/01691 filed Sep. 26, 1997.

5-$HT_{1A}$ ligands may be useful for the treatment of anxiety, depression and hypertension (Brain 5-$HT_{1A}$ Receptors: Behavioural and Neurochemical Pharmacology; Editors C. T. Dourish, S. Ahlenius, P. H. Huston; Ellis Horwod LTD, Chischester (1987)).

It has also been shown that 5-$HT_{1A}$ ligands inhibit the secretion of gastric acid (D. C. Evans, J. S. Gidda, *Gastroenterology,* 104, A76 (1993)), exhibit anti-emetic effects (F. Okada, Y. Torii, H. Saito, N. Matsuki, *Jpn. J. Pharmacol.,* 64, 109 (1994)) and act on the motility of the gastrointestinal system (Serotonin and Gastrointestinal Function, Editors T. S. Gaginella, J. J. Galligan; CRC Press, Boca Raton (1995)).

The present invention relates to new heteroaryloxyethylamines having a high affinity for the 5-$HT_{1A}$ receptor, a process for the preparation thereof, pharmaceutical compositions containing them, and their use particularly as inhibitors of gastric acid secretion or as anti-emetics.

A subject of the invention is, therefore, products corresponding to general formula I

I

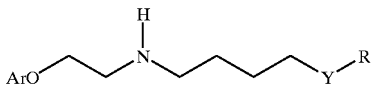

in which

- Ar represents a bicyclic heteroaryl, optionally substituted by one or more substituents;
- Y represents the radical —C(O)NH— or —NHC(O)—;
- R represents a lower alkyl radical; a cycloalkyl optionally substituted by one or more lower alkyl(s); or a phenyl optionally substituted by one or more substituents chosen from the hydroxy, cyano, halo, trifluoromethyl, lower alkyl, lower alkoxy radicals;
- and salts of said products.

More particularly, a subject of the invention is the products corresponding to general formula I as defined above, characterised in that Ar represents a bicyclic heteroaryl radical containing one or two nitrogen atoms, and the substituent(s) which the radical which Ar represents may bear are chosen from the hydroxy, nitro, halo, lower alkyl, lower alkoxy, lower alkyl carbonyl radicals.

In the definitions given above, the expression halo represents fluoro, chloro, bromo or iodo and preferably chloro. The expression lower alkyl represents a linear or branched alkyl radical having 1 to 6 carbon atoms, such as the methyl, ethyl, propyl, isopropyl, butyl, isobutyl, sec-butyl, tert-butyl, isopentyl, neopentyl and hexyl radicals.

The cycloalkyl radicals may be chosen from saturated monocyclic radicals having 3 to 7 carbon atoms such as the cyclopropyl, cyclobutyl, cyclopentyl, cyclohexyl and cycloheptyl radicals.

The lower alkoxy radicals may correspond to the lower alkyl radicals indicated above. Methoxy, ethoxy or isopropyloxy radicals are preferred.

The bicyclic heteroaryl radicals containing one or two nitrogen atoms may be chosen from the radicals corresponding to the compounds indole, indazole, isoquinoline, quinoline, quinoxaline and quinazoline.

The products corresponding to formula I may form addition salts with acids, particularly pharmacologically acceptable acids.

Examples of salts are given below in the experimental part.

More particularly, a subject of the invention is the products corresponding to general formula I as defined above, characterised in that Ar represents the quinolyl or quinoxalinyl radical, and the substituent(s) which the radical represented by Ar may bear are chosen from the hydroxy, chloro, methyl radicals.

More particularly, a subject of the invention is the products described below in the examples, particularly the products corresponding to the following formulae:

- N-[4-({2-(8-quinolyloxy)ethyl}amino)butyl]tert-butanamide,
- N-[4-({2-(8-quinolyloxy)ethyl}amino)butyl] neopentanamide,
- N-[4-({2-(8-quinolyloxy)ethyl}amino)butyl] cyclohexanamide,
- 4-methyl-N-[4-({2-(8-quinolyloxy)ethyl}amino)butyl] cyclohexanamide,
- N-[4-({2-(8-quinolyloxy)ethyl}amino)butyl]benzamide,
- N-[4-({2-(8-(5-chloro)quinolyloxy)ethyl}amino)butyl] neopentanamide,
- N-[4-({2-(8-(2-methyl)quinolyloxy)ethyl}amino)butyl] neopentanamide,
- N-[4-({2-(5-quinolyloxy)ethyl}amino)butyl]benzamide,
- N-[4-({2-(5-quinoxalyloxy)ethyl}amino)butyl]benzamide,
- N-[4-({2-(8-(2-hydroxy)quinolyloxy)ethyl}amino)butyl] benzamide,
- N-cyclohexyl-5-[(2-{8-quinolyloxy}ethyl)amino] pentanamide,
- N-neopentyl-5-[(2-{8-quinolyloxy}ethyl)amino] pentanamide,
- N-neopentyl-5-[(2-{5-quinoxalyloxy}ethyl)amino] pentanamide, and salts of said compounds with inorganic or organic acids.

The invention also provides a process for the preparation of the products corresponding to general formula I as defined above, characterised in that a product corresponding to formula II

II

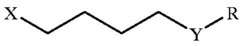

in which Y and R have the meaning given above and X represents a halogen or a pseudo halogen, is allowed to react with N-benzylethanolamine corresponding to the formula

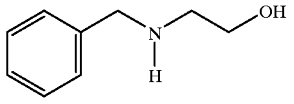

in order to obtain a product corresponding to formula III

III

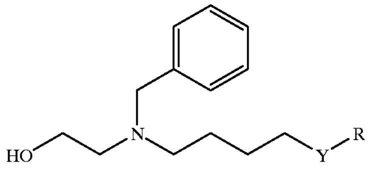

which is converted to a product corresponding to formula IV

IV

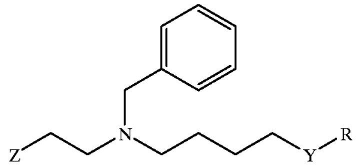

in which Z represents a halogen or a pseudo halogen, which product corresponding to formula IV is converted to a product corresponding to formula V

V

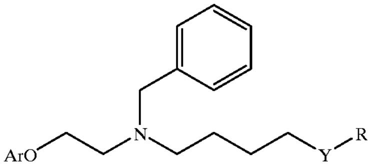

in which Ar has the meaning given above, the benzyl function of which product corresponding to formula V is cleaved in order to obtain the product corresponding to formula I, and which product corresponding to formula I may be converted to acid salts by the action of the corresponding acid.

In the syntheses as presented above, X and Z represent, independently, a leaving group such as chloro, bromo, iodo, methanesulfonyloxy, benzenesulfonyloxy or p-toluenesulfonyloxy, in other words, a halogen or pseudo halogen group.

Compounds corresponding to general formula III may be prepared by simply heating a compound corresponding to general formula II with an excess of N-benzylethanolamine in the absence of solvent, preferably under a nitrogen atmosphere and at a temperature between 70° C. and 85° C. Alternatively, the compounds corresponding to general formula III may be prepared by heating between 60° C. and 70° C. a compound corresponding to general formula II with N-benzylethanolamine in a polar solvent such as dimethylformamide, in the presence of an acid scavenger such as potassium carbonate and optionally in the presence of a catalyst such as potassium iodide.

The compounds corresponding to general formula III thus obtained may be converted, for example, to chlorides corresponding to general formula IV (Z=Cl) by reaction with methanesulfonyl chloride in an inert solvent such as dichloromethane, in the presence of an organic base such as triethylamine at ambient temperature.

Compounds corresponding to general formula V may be prepared from compounds corresponding to general formula IV by reacting these latter with an aryloxide anion produced from the appropriate hydroxyaryl derivative corresponding to formula ArOH, using either a base such as sodium hydride in a dipolar aprotic solvent such as dimethylformamide, or by heating to 80° C. compounds corresponding to general formula IV in a dipolar aprotic solvent such as dimethylformamide in the presence of a base, for example, an inorganic base, preferably potassium carbonate.

The compounds corresponding to general formula I are obtained by deprotecting the compounds corresponding to general formula V according to general known methods for N-debenzylation, for example, the reaction with a chloroformate such as α-chloroethylchloroformate followed by methanolysis, or catalytic hydrogenation in so far as this is compatible with the substituents on the aryl nucleus(nuclei) of the compounds corresponding to general formula V. Other methods of debenzylation as described in "Protective Groups in Organic Synthesis" [T. W. Green, P. G. M. Wuts; 2nd Edition., J. Wiley and Sons Inc., p. 364–6 (1991)] may also be used.

Optional conversion to salts of the products corresponding to formula I is also carried out according to the usual methods, for example, those indicated below in the experimental part.

The compounds of the present invention have advantageous pharmacological properties. It was thus discovered that the compounds of the present invention have a high affinity for the $5HT_{1A}$ receptor. The compounds of the present invention may thus be used in various therapeutic applications.

The compounds may inhibit the secretion of gastric acid. They may inhibit vomiting induced, for example, by cisplatin. Thus, the compounds of the invention may be used as anti-emetics or for the treatment of diseases in which it is necessary or desirable to reduce the secretion of gastric acid by, for example, gastric or duodenal ulcers, gastritis, gastro-oesophageal reflux, gastric dyspepsia, Zollinger-Ellison syndrome, nausea.

The compounds of the invention may also exhibit activity with respect to gastric emptying and intestinal motility. They may thus be used to combat constipation, post-operative atonia, gastroparesis.

They may also be used to combat certain diseases of the nervous system such as anxiety, depression, sleep disorders such as insomnia, dependence on certain drugs, Alzheimer's disease, dizziness, eating disorders such as anorexia. The compounds of the invention may also be used to treat diseases of the cardiovascular system, particularly hypertension.

An illustration of the pharmacological properties of the compounds of the invention will be found below in the experimental part.

Said properties render the products corresponding to formula I suitable for pharmaceutical use. The present application also provides, as medicaments, the products corresponding to formula I as defined above, and the addition salts with pharmaceutically acceptable inorganic or organic acids of said products corresponding to formula I, and pharmaceutical compositions containing, as active principle, at least one of the medicaments as defined above.

The invention also relates to pharmaceutical compositions containing a compound of the invention or an addition salt of pharmaceutically acceptable acid of the latter, in combination with a pharmaceutically acceptable carrier. The pharmaceutical composition may be in the form of a solid, for example, powders, granules, tablets, capsules or suppositories. Suitable solid carriers may be, for example, calcium phosphate, magnesium stearate, talc, sugars, lactose, dextrin, starch, gelatin, cellulose, methylcellulose, sodium carboxymethylcellulose, polyvinylpyrrolidone and wax.

The pharmaceutical compositions containing a compound of the invention may also be in the liquid form, for example, solutions, emulsions, suspensions or syrups. Suitable liquid carriers may be, for example, water, organic solvents such as glycerol or glycols and mixtures thereof, in various proportions, in water, added to pharmaceutically acceptable oils or fats. The sterile liquid compositions may be used for intramuscular, intraperitoneal or subcutaneous injections, and the sterile compositions may also be administered intravenously.

The invention also provides the use of products corresponding to formula I as defined above for the preparation of anti-emetic medicaments, medicaments intended to reduce gastric secretion, medicaments intended to accelerate gastric emptying, medicaments intended to modify intestinal transit, medicaments intended to treat anxiety, depression, sleep disorders and medicaments intended to treat cardiovascular diseases.

The invention also provides, as new industrial products, and particularly as new industrial products intended for the preparation of products corresponding to formula I, products corresponding to formulae V as described above.

The starting products of the invention are known products or which may be prepared from known products according to conventional methods known to the person skilled in the art. The following references may be cited: N-benzylethanolamine is a product sold, for example, by ACROS.

In the case where Y=NHC(O)—, the products corresponding to formula II may be prepared from ω-hydroxybutylamide according to conventional methods for the synthesis of halides or pseudo-halides: for example, in the case where X is a mesyl radical, these compounds II may be prepared according to the method described in *J. Org. Chem.,* 35 (9), 3195–6 (1970). The ω-hydroxybutylamide is itself obtained by condensation of the corresponding carboxylic acid or derivatives thereof such as the acid chloride with 4-amino-1-butanol (a product sold, for example, by ACROS) according to known methods.

In the case where Y=—C(O)NH—, the products corresponding to formula II may be obtained by the action of the corresponding amine having formula $RNH_2$ with a pentanoic acid having a halogen or pseudo halogen group in position 5, a bromine atom, for example, or an activated derivative of said acid such as the acid chloride, for example.

The compounds corresponding to formula ArOH are commercial products or may be prepared according to processes described in the literature (*J. Org. Chem.,* 33(3), 1089–92 (1968); *Helv. Chim. Acta* 34(2), 427–430 (1951).

The examples below are presented to illustrate the procedures above and should not in any case be regarded as limiting the scope of the invention.

EXPERIMENTAL PART

Example 1

N-[4-({2-(8-quinolyloxy)ethyl}amino)butyl] benzamide (I, Ar=8-quinolyl, R=phenyl, Y=—NHC(O)—: compound no. 5, Table 1)

First Step

N-[4-(benzyl-(2-hydroxyethyl)amino)butyl] benzamide (III, R=phenyl, Y=—NHC(O)—)

A mixture of N-benzylethanolamine (60.5 g, 56.8 ml, 0.4 mole) and N-[4-(methanesulfonyloxy)butyl]benzamide (51.5 g, 0.19 mole) is heated for 2 hours at 75–80° C. under a nitrogen atmosphere. The reaction mixture is cooled, taken up in dichloromethane (400 ml), the solution is washed with water (3×100 ml), then dried over magnesium sulfate. The solution is filtered and the solvent removed under reduced pressure in order to obtain an oil which crystallises with diisopropylether. 51.5 g (83%) of the desired compound are obtained in the form of white crystals, m.p.=61–62° C.

Second Step

N-[4-(benzyl-(2-chloroethyl)amino)butyl]benzamide (IV, R=phenyl, Y=—NHC(O)—)

Methanesulfonyl chloride (14.8 g, 10 ml, 0.13 mole) is added dropwise, with stirring, to a cooled solution (5° C.) of N-[4{benzyl(2-hydroxyethyl)amino}butyl]benzamide (35 g, 0.11 mole) in dichloromethane (300 ml). The solution is brought back to ambient temperature and, after 1.5 hour, triethylamine is added (13 g, 18 ml, 0.13 mole) and agitation is maintained for another 1.5 hour. The reaction mixture is washed with iced water (150 ml), with saturated salted water (2×100 ml) and dried over magnesium sulfate. Filtration and evaporation of the solvent under reduced pressure give 36.6 g (99%) of the expected compound in the form of a clear maroon oil which crystallises if kept at 4° C.

NMR—$^1$H ($CDCl_3$),: 1.58–1.67 (m, 4H), 2.58 (m, 2H), 2.83 (t, 2H, J=6.8 Hz), 3.40–3.45 (q, 2H, J=6.5 Hz), 3.51 (t, 2H, J=6.8 Hz), 3.66 (s, 2H), 6.19 (s, 1H), 7.24–7.48 (m, 8H), 7.73–7.75 (m, 2H).

Third Step

N-[4-(benzyl-(2- {8-quinolyloxy}ethyl)amino)butyl] benzamide (V, Ar=8-quinolyl, R=phenyl, Y=—NHC(O)—)

Sodium hydride (0.63 g, 16 mmole) is added in portions with stirring to a cooled solution (5° C.) of 8-hydroxyquinoline (2.3 g, 16 mmole) in anhydrous dimethylformamide (80 ml). The solution is agitated for 30 minutes at ambient temperature (25° C.), then N-[4-{benzyl (2-chloroethyl)amino}butyl]benzamide (5 g, 14 mmole) in solution in anhydrous dimethylformamide (80 ml) is added dropwise. The reaction mixture is kept at 60° C. for 2 hours then the solvent is evaporated under reduced pressure. The residue is taken up in dichloromethane (100 ml), then washed with water and dried over magnesium sulfate. Filtration and evaporation of the solvent under reduced pressure give an oil which is purified by flash chromatography over silica gel using a mixture of ethyl acetate/heptane (2/1) as eluant to obtain 6.1 g (95%) of the desired compound in the form of an oil.

NMR—$^1$H (DMSO),: 1.50–1.70 (m, 4H), 2.54–2.61 (m, 2H), 2.93 (t, 2H, J=5 Hz), 3.24–3.30 (m, 2H), 3.73 (s, 2H), 4.25 (t, 2H, J=5 Hz), 7.00–7.60 (m=10H), 7.70–7.90 (m, 2H), 8.30 (dd, 1H, $J_1$=2 Hz, $J_2$=12 Hz), 8.45 (t, 2H, J=7 Hz) 8.85 (dd, 1H, $J_1$=2 Hz, $J_2$=4 Hz).

Fourth Step

N-[4-({2-(8-quinolyloxy)ethyl}amino)butyl] benzamide

A solution of -chloroethylchloroformate (1.9 ml, 2.5 g, 17.5 mmole) in dry 1,2-dichloroethane (10 ml) is added dropwise to a solution of N-[4-{benzyl[2-(8-quinoleinoxy)

ethyl]amino}butyl]benzamide (4 g, 8.8 mmole) in dry 1,2-dichloroethane (40 ml) under a nitrogen atmosphere and at 5° C. After one hour's heating at 60° C., the solvent is evaporated under reduced pressure, the residue is taken up in methanol (40 ml) and heated for one hour under reflux. The solvent is concentrated under reduced pressure then the residue is taken up in dichloromethane (50 ml) and water (50 ml). The aqueous phase is collected and converted to a base by a saturated solution of sodium hydrogen carbonate then the product is extracted by 3 washes with dichloromethane (30 ml). After evaporation of the solvent, the residue is purified by flash chromatography over silica gel in a mixture of dichloromethane/methanol (90/10) to which had been added a few drops of triethylamine. 1.8 g (58%) of the desired product is obtained in the form of a colourless oil.

Treatment of an ethanolic solution of this free base (1.7 g) with a hot solution of fumaric acid (0.57 g) gives 1.5 g of the fumarate of compound No. 5 in the form of white crystals, m.p.=144–149° C.

NMR—$^1H$ (DMSO),: 1.60 (m, 4H), 3.00 (t, 2H J=7.4 Hz), 3.30 (m, 4H), 4.40 (t, 2H, J=7.4 Hz), 6.50 (s, 2H), 7.30 (dd, 1H, $J_1$=1.3 Hz, $J_2$=6.23 Hz), 7.40–7.60 (m, 6H), 7.85 (dd, 2H), 8.35 (dd, 1H), 8.55 (t, 1H), 8.90 (dd, 1H).

NMR—$^{13}C$ (DMSO),: 24.53; 26.55; 46.46; 47.64; 66.55; 112.73; 120.66; 121.98; 126.45; 127.09; 128.39; 129.10; 131.29; 134.64; 136.13; 139.82; 149.35; 153.88; 166.15; 167.59.

IR (Nujol), $cm^{-1}$: 3302 (NH), 1709 (C═O), 1630 (C═O), 1577 (C═C), 1546 (C—N)

Example 2

N-cylohexyl-5-[(2-{8-quinolyloxy}ethyl)amino] pentanamide (I, Ar=8-quinolyl, R=cyclohexyl, Y=—C(O)NH—: compound no. 11, Table 1)

First Step

N-cyclohexyl-5-[benzyl-(2-hydroxyethyl)amino] pentanamide (III, R=cyclohexyl, Y=—C(O)NH—)

A mixture of N-benzylethanolamine (10.14 g, 67 mmole), potassium carbonate (18.53 g, 134 mmole) and potassium iodide (0.5 g, 3 mmole) in suspension in dry dimethylformamide (100 ml) is heated to 60° C. for 15 minutes. A solution of N-cyclohexyl-5-bromopentanamide (17.6 g, 67 mmole) in dimethylformamide (35 ml) is then added dropwise. The reaction medium is kept under agitation at this temperature for 2 hours. The solids in suspension are filtered, then ethyl acetate (70 ml) and water (60 ml) are added to the medium. The organic phase is collected, dried over sodium sulfate. After filtration and evaporation of the solvents under reduced pressure, the product obtained in the form of an oil is purified by flash chromatography over silica gel in an eluant of dichloromethane/methanol/ammonia (90/10/1) in order to obtain 12.7 g (57%) of the desired product in the form of a colourless oil.

NMR—$^1H$ ($CDCl_3$),: 1.00–1.90 (m, 14H), 2.05 (t, 2H, J=6.4 Hz), 2.40–2.65 (m, 4H), 3.50–3.85 (m, 5H), 5.30 (m, 1H), 7.30 (s, 5H).

Second Step

N-cyclohexyl-5-[benzyl-(2-chloroethyl)amino] pentanamide (IV, R=cyclohexyl, Y=—C(O)NH—)

A solution of methanesulfonyl chloride (3.8 g, 2.56 ml, 33 mmole) in dichloromethane (30 ml) is added dropwise, with stirring, to a cooled solution (5° C.) of N-cyclohexyl-5-{benzyl(2-hydroxyethyl)amino}pentanamide (9.15 g, 27.5 mmole) in dichloromethane (30 ml) in the presence of triethylamine (3.62 g, 5 ml, 36 mmole). The reaction is kept at 20° C. for one hour, then the reaction mixture is washed with iced water (50 ml) and dried over sodium sulfate. Filtration and evaporation of the solvent under reduced pressure give 9.60 g (99%) of the desired compound in the form of a yellow oil which is used for the next step without any other purification.

Third Step

N-cyclohexyl-5-[benzyl-(2-{8-quinolyloxy}ethyl) amino]pentanamide

V, Ar=8-quinolyl, R=cyclohexyl, Y=—C(O)NH—)

Sodium hydride (0.23 g, 5.7 mmole) is added in portions with stirring to a cooled solution (5° C.) of 8-hydroxyquinoline (0.83 g, 5.7 mmole) in anhydrous dimethylformamide (10 ml). The solution is agitated for 15 minutes at 20° C. then N-cyclohexyl-4-{benzyl(2-chloroethyl)amino}butanamide (2 g, 5.7 mmole) in solution in anhydrous dimethylformamide (10 ml) is added dropwise. The reaction mixture is kept at 50° C. for 3 hours then ethyl acetate (10 ml) and water (10 ml) are added to the medium. The organic phase is collected then washed with a 1 N sodium hydroxide solution, and dried over sodium sulfate. After filtration and evaporation, the expected product is purified by flash chromatography over silica gel in a mixture of dichloromethane/methanol (95/5). 1.1 g (41%) of product is obtained in the form of a colourless oil.

Fourth Step

N-cyclohexyl-5-[(2-{8-quinolyloxy}ethyl)amino] pentanamide

A solution of -chloroethylchloroformate (0.67 g, 0.51 ml, 4.7 mmole) in dry 1,2-dichloroethane (3 ml) is added dropwise to a solution of N-cyclohexyl-5-{benzyl[2-(8-quinoleinoxy)ethyl]amino}pentanamide (1.08 g, 2.35 mmole) in dry 1,2-dichloroethane (10 ml) under a nitrogen atmosphere and at 5° C. After two hours' heating at 40° C., the solvent is evaporated under reduced pressure, the residue is taken up in methanol (30 ml) and heated for 30 minutes under reflux. The solvent is concentrated under reduced pressure then the residue is taken up in dichloromethane (30 ml) and washed with a 2N sodium hydroxide solution. The organic phase is collected then dried over sodium sulfate. After filtration and evaporation of the solvent, the product is purified by flash chromatography over silica gel in a mixture of dichloromethane/methanol/ammonia (80/20/2). The product is obtained in the form of a colourless oil (0.24 g, 28%).

Treatment of a solution of this free base (0.2 g) in acetone with an acetone solution of fumaric acid gives the fumarate of compound no.11 (0.12 g) in the form of beige crystals, m.p.=113–119° C.

NMR—$^1H$ (DMSO),: 1.00–1.30 (m, 5H), 1.50–1.75 (m, 10H), 2.10 (t, 2H, J=6.4 Hz), 3.00 (t, 2H, J=7.2 Hz), 3.30 (t, 2H, J=5.2 Hz), 3.50 (m, 1H), 4.40 (t, 2H, J=5.2 Hz), 6.50 (s, 2H), 7.30 (d, 1H, J=7.2 Hz), 7.55 (m, 3H), 7.70 (d, 1H, J=7.8 Hz), 8.35 (dd, 1H, $J_1$=1.3 Hz, $J_2$=8.2 Hz), 8.85 (dd, 1H, $J_1$=1.4 Hz, $J_2$=4 Hz).

NMR—$^{13}C$ (DMSO),: 22.89; 24.79; 25.42; 26.32; 32.71; 35.12; 46.37; 47.47; 47.64; 66.44; 111.36; 120.87; 122.16;

127.05; 129.32; 135.11; 136.28; 140.00; 149.36; 153.99; 167.76; 170.90.

IR (Nujol), $cm^{-1}$: 3308 (N—H), 1704 (C═O), 1641 (C═O), 1540 (C—N)

The processes described above give a compound of the invention in the form of a free base or an addition salt with an acid. If the compound of the invention is obtained in the form of an addition salt with an acid, the free base may be obtained by converting a solution of the addition salt to a base with a base. Conversely, if the product of the process is a free base, the addition salt with an acid, particularly an addition salt with a pharmaceutically acceptable acid, may be obtained by dissolving the free base in an appropriate organic solvent and treating the solution with an acid, according to conventional procedures for the preparation of addition salts with an acid from free bases.

Examples of addition salts with an acid are those derived from inorganic acids such as sulfuric, hydrochloric, hydrobromic or phosphoric acid, or organic acids such as tartaric, fumaric, maleic, citric, caprylic, benzoic, methanesulfonic, p-toluenesulfonic, benzenesulfonic, succinic or acetic acid.

As regards the compounds of the invention containing an asymmetrical centre, the racemic mixtures and the individual optically active isomers are also considered to be part of the scope of the invention.

Table 1 below shows the main compounds prepared according to the above procedures and which illustrate the invention without limiting its scope. Compounds nos. 5 and 11 correspond respectively to the products of examples 1 and 2 described above. The other products were prepared using the same process.

TABLE 1

| Compound No. | Ar | Y | R | Salt | m.p. (° C.) |
|---|---|---|---|---|---|
| 1 | 8-quinolyl | —NHC(O)— | tert-butyl | fumarate | 141–143.5 |
| 2 | 8-quinolyl | —NHC(O)— | neopentyl | fumarate | 110.5–111 |
| 3 | 8-quinolyl | —NHC(O)— | cyclohexyl | fumarate | 125–127.5 |
| 4 | 8-quinolyl | —NHC(O)— | 1-methyl-cyclohexyl | fumarate | 113.5–114.5 |
| 5 | 8-quinolyl | —NHC(O)— | phenyl | fumarate | 146–149 |
| 6 | 5-Cl-8-quinolyl | —NHC(O)— | neopentyl | 1,5-fumarate | 122.5–125 |
| 7 | 2-Me-8-quinolyl | —NHC(O)— | neopentyl | fumarate | 95–97 |
| 8 | 5-quinolyl | —NHC(O)— | phenyl | hemifumarate | 168–170 |
| 9 | 5-quinoxalyl | —NHC(O)— | phenyl | dichlorohydrate | 178–180 |
| 10 | 2-OH-8-quinolyl | —NHC(O)— | phenyl | hemifumarate | 177–180 |
| 11 | 8-quinolyl | —C(O)NH— | cyclohexyl | fumarate | 113–119 |
| 12 | 8-quinolyl | —C(O)NH— | neopentyl | fumarate | 109.5–111 |
| 13 | 5-quinoxalyl | —C(O)NH— | neopentyl | 0.75-fumarate | 131–133 |

Using the process indicated above, it is also possible to prepare the following products, which are also part of the invention:

| Compound | Ar | Y | R |
|---|---|---|---|
| A | 8-quinolyl | —C(O)NH— | phenyl |
| B | 5-quioxalyl | —C(O)NH— | 4-chlorophenyl |
| C | 5-F-8-quinolyl | —C(O)NH— | cyclohexyl |
| D | 5-isoquinolyl | —C(O)NH— | methyl |
| E | 8-Me-7-isoquinolyl | —C(O)NH— | cyclopentyl |
| F | 8-quinolyl | —C(O)NH— | 4-methylcyclohexyl |
| G | 8-Me-7-isoquinolyl | —C(O)NH— | cycloheptyl |

-continued

| Compound | Ar | Y | R |
|---|---|---|---|
| H | 5-quinoxalyl | —NHC(O)— | 3-methoxyphenyl |
| I | 5-isoquinolyl | —NHC(O)— | cyclopentyl |
| J | 5-isoquinolyl | —NHC(O)— | propyl |

Pharmacological Study of the Products of the Invention

Affinity of the Compounds of the Invention for the 5-$HT_{1A}$ Receptor

The affinity of the compounds for serotonergic 5-$HT_{1A}$ receptors is determined by measuring the inhibition of [3H]8-hydroxy-2(di-n-propylamino)tetralin([3H]8-OH-DPAT) bound to the cerebral cortex of the rat, according to the method of Peroutka and his coworkers [(*J. Neurochem.,* 47, 529 (1986)].

Cerebral cortices of male Sprague Dawley rats are homogenised in Tris-HCl 50 mM, pH=7.4 and centrifuged at 40,000 g for 10 min at 4° C. Pellets are resuspended in the same buffer and incubated for 10 min at 37° C., and the homogenised products are centrifuged again at 40,000 g for 10 min at 4° C.

Competitive inhibition tests of [3H]8-OH-DPAT binding are carried out three times with unlabelled competitors, with concentrations between 100 pM and 100 M. Cerebral cortex membranes of rats (10 mg wet weight/ml) are incubated with [3H]8-OH-DPAT (1 nM) for 30 min at 25° C. in Tris-HCl 50 mM, pH=7.4 containing 4 mM of $CaCl_2$, 10 M of pargyline and 0.1% of ascorbic acid.

The bound [3H]8-OH-DPAT is separated from free [3H] 8-OH-DPAT by immediate filtration by means of Whatman GF/B glass fibre filters using a Brandel cell recovery device. The filters are washed three times with the same buffer at 0–4° C. and their radioactivity is studied by means of a liquid scintillation spectrometer.

The specific binding is obtained by subtracting the binding determined in the presence of 1 M of 8-OH-DPAT from the total binding. The characteristics of the binding are analysed by iterative analysis of the non-linear regression by computer, using the Ligand program [Munson and Rodbard, *Anal. Biochem.,* 107, 220 (1980)].

The results for the compounds which are representative of the invention are given in Table 2 below.

TABLE 2

| Compound No. | Ki (nM) |
|---|---|
| 1 | 0.081 |
| 2 | 0.12 |
| 3 | 0.15 |
| 4 | 0.11 |
| 5 | 0.055 |
| 6 | 0.98 |
| 7 | 0.35 |
| 9 | 0.75 |
| 11 | 0.072 |
| 12 | 0.09 |
| 13 | 0.48 |

What is claimed is:

1. A compound selected from the group consisting of a compound of the formula

I

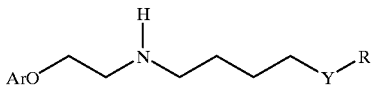

wherein Ar is a bicyclic heteroaryl unsubstituted or substituted with at least one member of the group consisting of —OH, $NO_2$, halogen alkyl of 1 to 6 carbon atoms, alkoxy of 1 to 6 carbon atoms and a alkylcarbonyl of 2 to 7 carbon atoms, Y is

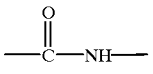

or

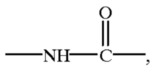

R is selected from the group consisting of alkyl of 1 to 6 carbon atoms, cycloalkyl of 3 to 7 carbon atoms, unsubstituted or substituted with at least one alkyl of 1 to 6 carbon atoms and phenyl unsubstituted or substituted by at least one member of the group consisting of —OH, —CN, halogen, —$CF_3$, alkyl of 1 to 6 carbon atoms and alkoxy of 1 to 6 carbon atoms and its non-toxic, pharmaceutically acceptable acid addition salts.

2. A compound of claim 1 wherein Ar is a bicyclic heteroaryl with one or two nitrogens.

3. A compound of claim 1 wherein Ar is quinoyl or quinoxalynyl unsubstituted or substituted with at least one member of the group consisting of —OH, —$CH_3$ and chloro.

4. A compound of claim 1 selected from the group consisting of:

N-[4-({2-(8-quinolyloxy)ethyl}amino)butyl]tert-butanamide,

N-[4-({2-(8-quinolyloxy)ethyl}amino)butyl] neopentanamide,

N-[4-({2-(8-quinolyloxy)ethyl}amino)butyl] cyclohexanamide, 4-methyl-N-[4-({2-(8-quinolyloxy)ethyl}amino)butyl] cyclohexanamide, N-[4-({2-(8-quinolyloxy)ethyl}amino)butyl]benzamide, N-[4-({2-(8-(5-chloro)quinolyloxy)ethyl}amino)butyl] neopentanamide, N-[4-({2-(8-(2-methyl)quinolyloxy)ethyl}amino)butyl] neopentanamide, N-[4-({2-(5-quinolyloxy)ethyl}amino)butyl]benzamide, N-[4-({2-(5-quinoxalyloxy)ethyl}amino)butyl]benzamide, N-[4-({2-(8-(2-hydroxy)quinolyloxy)ethyl}amino)butyl] benzamide, N-cyclohexyl-5-[(2-{8-quinolyloxy}ethyl)amino] pentanamide, N-neopentyl-5-[(2-{8-quinolyloxy}ethyl)amino] pentanamide, N-neopentyl-5-[(2-{5-quinoxalyloxy}ethyl)amino] pentanamide, and salts of said compounds with inorganic or organic acids.

5. A process for the preparation of a compound of claim 1 comprising reacting a compound of formula

II

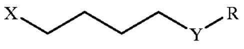

wherein Y and R have the definitions of claim 1 and X is halogen or pseudo halogen with N-benzylethanolamine to obtain a compound of the formula

III

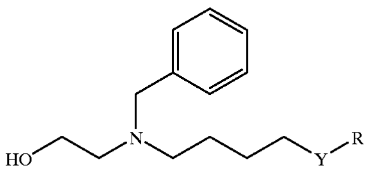

reacting the latter with a halogenating or pseudo-halogenating agent to obtain a compound of the formula

IV

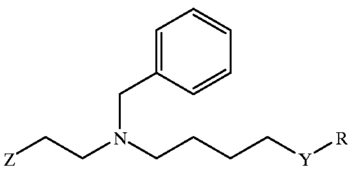

wherein Z is halogen or pseudo halogen, reacting the latter with an Ar oxide anion to obtain a compound of the formula

V

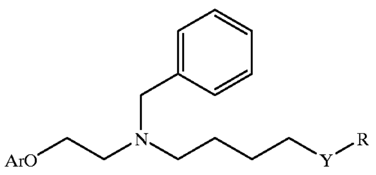

and reacting the latter with a N-debenzylating agent to form a compound of formula I.

6. An anti-hypertensive composition comprising an anti-hypertensively effective amount of a compound of claim 1 and an inert pharmaceutical carrier.

7. An anti-hypertensive composition comprising an anti-hypertensively effective amount of a compound of claim 4 and an inert pharmaceutical carrier.

8. A compound of formula V as defined in claim 5.

9. A method of inhibiting gastric secretion in warm-blooded animals comprising administering to warm-blooded animals an antigastric secretion effective amount of a compound of claim 1.

10. A method of treating hypertension in warm-blooded animals comprising administering to warm-blooded animals an anti-hypertensively effective amount of a compound of claim 1.

* * * * *